(12) United States Patent
Hagihara

(10) Patent No.: US 10,610,619 B2
(45) Date of Patent: Apr. 7, 2020

(54) IMAGING DEVICE FOR ENDOSCOPE, AND METHOD OF MANUFACTURING IMAGING DEVICE FOR ENDOSCOPE

(71) Applicant: Sony Olympus Medical Solutions Inc., Tokyo (JP)

(72) Inventor: Masahiro Hagihara, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 392 days.

(21) Appl. No.: 15/702,784

(22) Filed: Sep. 13, 2017

(65) Prior Publication Data
US 2018/0085495 A1    Mar. 29, 2018

(30) Foreign Application Priority Data
Sep. 23, 2016 (JP) .................. 2016-186262

(51) Int. Cl.
| | |
|---|---|
| G02B 7/02 | (2006.01) |
| A61L 29/02 | (2006.01) |
| G02B 23/24 | (2006.01) |
| A61B 1/00 | (2006.01) |
| A61L 29/14 | (2006.01) |

(52) U.S. Cl.
CPC .......... *A61L 29/02* (2013.01); *A61B 1/0011* (2013.01); *A61B 1/00096* (2013.01); *A61L 29/14* (2013.01); *G02B 23/2484* (2013.01); *G02B 23/2492* (2013.01)

(58) Field of Classification Search
CPC ....................................................... A61L 29/02
USPC ............................................................ 359/820
See application file for complete search history.

(56) References Cited

U.S. PATENT DOCUMENTS

2015/0257631 A1* 9/2015 Sasamoto ............... A61B 1/04
250/216

FOREIGN PATENT DOCUMENTS

JP    2004-167083    6/2004

* cited by examiner

*Primary Examiner* — James C. Jones
(74) *Attorney, Agent, or Firm* — Xsensus LLP

(57) ABSTRACT

An imaging device includes: an optical element including a metal layer adapted to be brazed and arranged on an outer peripheral surface of the optical element; a first frame body including a metal part adapted to be brazed and arranged at least on an inner peripheral surface and an outer peripheral surface of the first frame body, the inner peripheral surface being brazed onto the outer peripheral surface of the optical element; and a second frame body including a metal part adapted to be brazed and arranged at least on an inner peripheral surface of the second frame body, the inner peripheral surface being brazed onto the outer peripheral surface of the first frame body. A coefficient of thermal expansion of the first frame body is closer to a coefficient of thermal expansion of the optical element than a coefficient of thermal expansion of the second frame body.

6 Claims, 8 Drawing Sheets

IMAGING DEVICE FOR ENDOSCOPE, AND METHOD OF MANUFACTURING IMAGING DEVICE FOR ENDOSCOPE

CROSS-REFERENCE TO RELATED APPLICATION

The present application claims priority to and incorporates by reference the entire contents of Japanese Patent Application No. 2016-186262 filed in Japan on Sep. 23, 2016.

BACKGROUND

The present disclosure relates to an imaging device for an endoscope and a method of manufacturing the imaging device for an endoscope.

In the related art of a medical field, there is known an endoscope device for imaging a subject such as the inside of a living body using an imaging element, and observing the subject (for example, refer to Japanese Laid-open Patent Publication No. 2004-167083).

The endoscope device disclosed in Japanese Laid-open Patent Publication No. 2004-167083 includes an insertion part (endoscope) that is inserted into a living body to capture a subject image, and an imaging device for an endoscope that is detachably connected to an eyepiece part of the insertion part to take the subject image captured by the insertion part.

Such an imaging device for an endoscope is autoclaved (high-temperature and high-pressure steam sterilization treatment) or disinfected by wiping or immersion before use. That is, the imaging device for an endoscope needs to be configured so that high-temperature and high-pressure steam in autoclave treatment and a medical fluid used for disinfection treatment by wiping or immersion hardly enter the inside of the imaging device for an endoscope.

Thus, in the imaging device for an endoscope disclosed in Japanese Laid-open Patent Publication No. 2004-167083, an imaging element and the like are arranged in airtight packaging having a tubular shape, an opening at one end of the airtight packaging is airtightly sealed by brazing with an optical element (sapphire window), and an opening at the other end thereof is airtightly sealed by brazing with a hermetic connector.

SUMMARY

FIG. 9 is a diagram for explaining a problem about an imaging device 100 for an endoscope in the related art. Specifically, FIG. 9A is a diagram illustrating a state of one end of the imaging device 100 for an endoscope in brazing. FIG. 9B is a diagram illustrating a state of one end of the imaging device 100 for an endoscope after brazing. FIGS. 9A and 9B are cross-sectional views obtained by cutting airtight packaging 101 and an optical element 102 on a plane including a center axis Ax0 of the airtight packaging 101.

The airtight packaging 101 is configured of metal such as stainless steel. On an inner peripheral side of one end of the airtight packaging 101, a recessed part 1011 is arranged being recessed from the one end toward the other end into which the optical element 102 is loosely fitted.

On the other hand, the optical element 102 is configured of sapphire glass having a flat plate shape. A metal layer 1021 that may be brazed is arranged on an outer peripheral surface of the optical element 102.

As illustrated in FIG. 9A, the optical element 102 is fixed to the recessed part 1011 by brazing (soldering) using solder SD in a state of being loosely fitted into the recessed part 1011. Accordingly, an opening at one end of the airtight packaging 101 is sealed by the optical element 102.

In this case, there is a difference in a coefficient of thermal expansion between the airtight packaging 101 and the optical element 102. Thus, when brazing is performed (FIG. 9A) in a high temperature environment of approximately 300° C. and the temperature is returned to the ordinary temperature, distortion is caused in the optical element 102 due to the difference in the coefficient of thermal expansion between the members 101 and 102 as illustrated in FIG. 9B. In this way, when distortion is caused in the optical element 102, the subject image may not be favorably taken by the imaging element, and image quality is deteriorated in some cases.

Thus, there is a demand for a technique of reducing distortion in the optical element.

An imaging device for an endoscope according to one aspect of the present disclosure includes: an optical element including a metal layer adapted to be brazed and arranged on an outer peripheral surface of the optical element; a first frame body including a metal part adapted to be brazed and arranged at least on an inner peripheral surface and an outer peripheral surface of the first frame body, the inner peripheral surface being brazed onto the outer peripheral surface of the optical element; and a second frame body including a metal part adapted to be brazed and arranged at least on an inner peripheral surface of the second frame body, the inner peripheral surface being brazed onto the outer peripheral surface of the first frame body, wherein a coefficient of thermal expansion of the first frame body is closer to a coefficient of thermal expansion of the optical element than a coefficient of thermal expansion of the second frame body.

DETAILED DESCRIPTION

Figure 1:
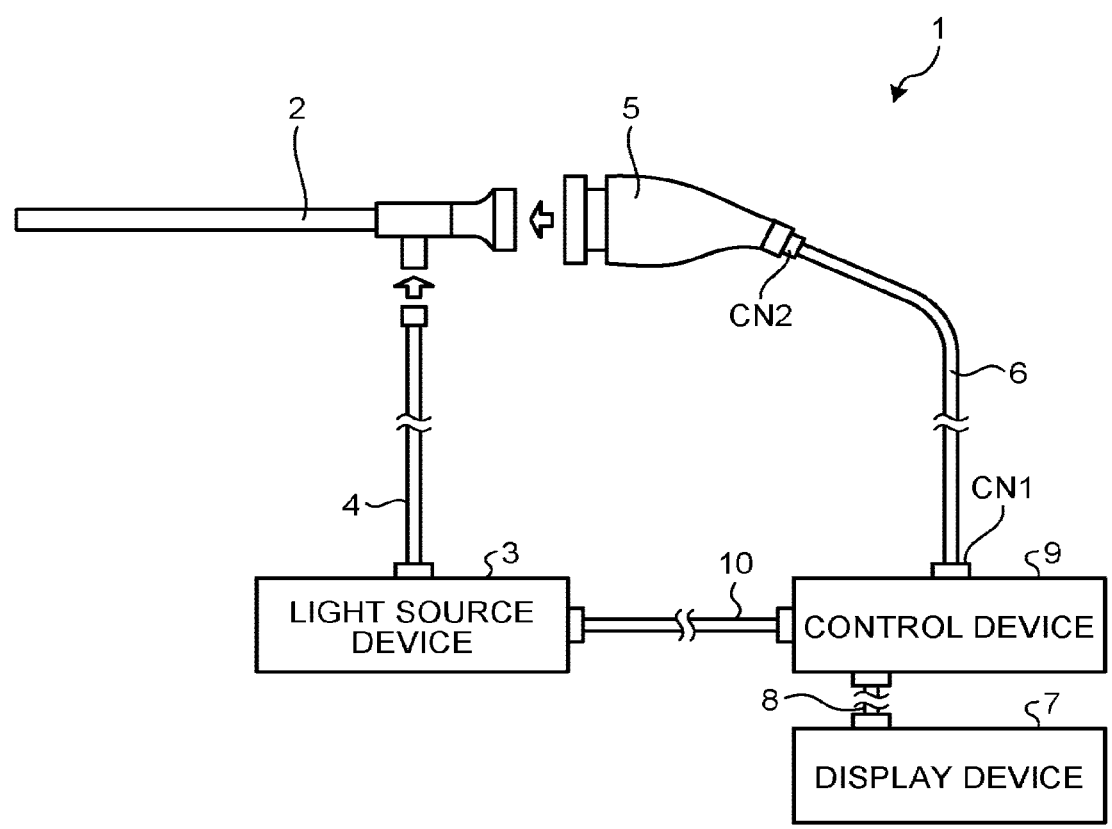
FIG. 1 is a diagram illustrating a schematic configuration of an endoscope device according to a first embodiment of the present disclosure.

The following describes modes for carrying out the present disclosure (hereinafter, referred to as embodiments) with reference to the drawings. The present disclosure is not limited to the embodiments described below. The same component is denoted by the same reference numeral throughout description about the drawings.

First Embodiment

Schematic Configuration of Endoscope Device

FIG. 1 is a diagram illustrating a schematic configuration of an endoscope device 1 according to a first embodiment of the present disclosure.

The endoscope device 1 is a device used in a medical field for observing a subject such as the inside of a living body. As illustrated in FIG. 1, the endoscope device 1 includes an insertion part 2, a light source device 3, a light guide 4, an imaging device 5 for an endoscope, a first transmission cable 6, a display device 7, a second transmission cable 8, a control device 9, and a third transmission cable 10.

The insertion part 2 is hard, or at least part thereof is soft, and has a long and narrow shape to be inserted into a living body. An optical system is arranged in the insertion part 2, the optical system being configured of one or a plurality of lenses to condense light of a subject image.

One end of the light guide 4 is connected to the light source device 3, and the light source device 3 supplies light for illuminating the inside of the living body to the one end of the light guide 4 under control by the control device 9.

One end of the light guide 4 is detachably connected to the light source device 3, and the other end thereof is detachably connected to the insertion part 2. The light guide 4 then transfers the light supplied from the light source device 3 from the one end to the other end to be supplied to the insertion part 2. The light supplied to the insertion part 2 is emitted from a distal end of the insertion part 2, and applied to the inside of the living body. The light (subject image) applied to the inside of the living body is condensed by the optical system within the insertion part 2.

The imaging device 5 for an endoscope is detachably connected to a base end (eyepiece part) of the insertion part 2. The imaging device 5 for an endoscope takes the subject image the light of which is condensed by the insertion part 2 under control by the control device 9, and outputs an imaging signal (image signal) obtained through the imaging.

A detailed configuration of the imaging device 5 for an endoscope will be described later.

One end of the first transmission cable 6 is detachably connected to the control device 9 via a connector CN1 (FIG. 1), and the other end thereof is connected to the imaging device 5 for an endoscope via a connector CN2 (FIG. 1). The first transmission cable 6 transmits an image signal output from the imaging device 5 for an endoscope to the control device 9, and transmits a control signal, a synchronizing signal, a clock, electric power, and the like output from the control device 9 to the imaging device 5 for an endoscope.

In transmission of the image signal from the imaging device 5 for an endoscope to the control device 9 via the first transmission cable 6, the image signal may be transmitted as an optical signal, or may be transmitted as an electric signal. The same applies to transmission of the control signal, the synchronizing signal, and the clock from the control device 9 to the imaging device 5 for an endoscope via the first transmission cable 6.

The display device 7 is configured with a display using a liquid crystal, organic EL (Electro Luminescence), or the like.

One end of the second transmission cable 8 is detachably connected to the display device 7, and the other end thereof is detachably connected to the control device 9. The second transmission cable 8 transmits a video signal processed by the control device 9 to the display device 7.

The control device 9 includes a central processing unit (CPU) and the like, and comprehensively controls operations of the light source device 3, the imaging device 5 for an endoscope, and the display device 7.

Specifically, the control device 9 generates the video signal by performing predetermined processing on the image signal acquired from the imaging device 5 for an endoscope via the first transmission cable 6, and outputs the video signal to the display device 7 via the second transmission cable 8. The display device 7 displays an image for observation based on the video signal. The control device 9 outputs the control signal and the like to the imaging device 5 for an endoscope or the light source device 3 via the first transmission cable 6 or the third transmission cable 10.

One end of the third transmission cable 10 is detachably connected to the light source device 3, and the other end thereof is detachably connected to the control device 9. The third transmission cable 10 transmits the control signal from the control device 9 to the light source device 3.

Configuration of Imaging Device for Endoscope

Next, the following describes a configuration of the imaging device 5 for an endoscope.

Figure 2:
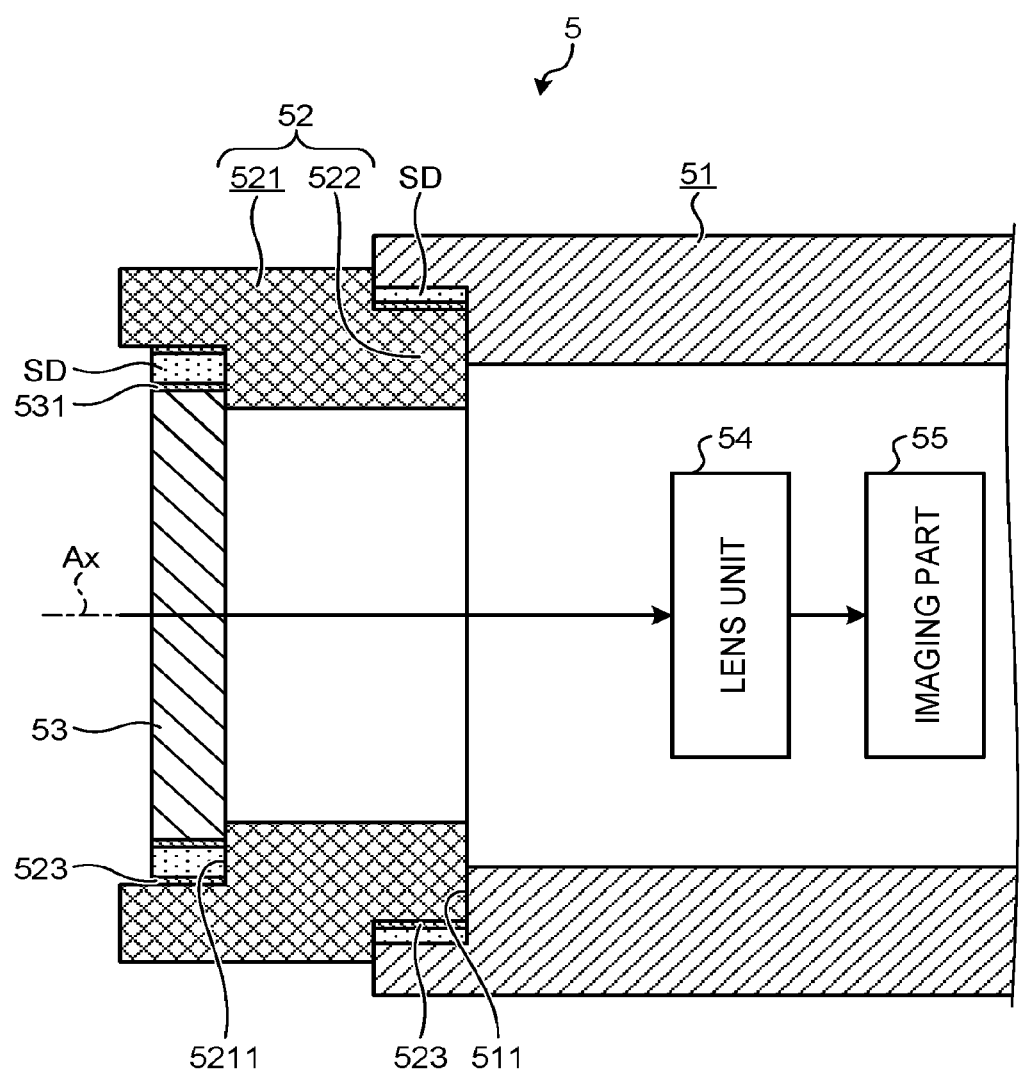
FIG. 2 is a diagram schematically illustrating a configuration of an imaging device for an endoscope illustrated in FIG. 1.

FIG. 2 is a diagram schematically illustrating the configuration of the imaging device 5 for an endoscope.

In the following description, "one end" means an end to which the base end (eyepiece part) of the insertion part 2 is connected. The "other end" means an end to which the first transmission cable 6 is connected.

As illustrated in FIG. 2, the imaging device 5 for an endoscope includes a casing 51, an optical element holding member 52, an optical element 53, a lens unit 54, and an imaging part 55.

The casing 51 has a function as a second frame body according to the present disclosure. The casing 51 has a tubular shape (for example, a cylindrical shape) having openings at one end and the other end thereof. The lens unit 54 and the imaging part 55 are housed inside the casing 51.

As illustrated in FIG. 2, a first recessed part 511 is formed on an inner peripheral side of the one end of the casing 51, the first recessed part 511 being recessed from the one end toward the other end into which the optical element holding member 52 is loosely fitted.

In the first embodiment, the casing 51 is configured of SUS304 (coefficient of thermal expansion: $17 \times 10^{-6}/°$ C.) having chemical resistance.

To the other end of the casing 51, a hermetic connector (not illustrated) is fixed by brazing, the hermetic connector being detachably connected to the connector CN2 of the first transmission cable 6 and electrically connected to the imaging part 55. That is, the opening at the other end of the casing 51 is airtightly sealed by the hermetic connector.

The optical element holding member 52 is a member that holds the optical element 53 and fixes the optical element 53 to the casing 51, and has a function as a first frame body according to the present disclosure. As illustrated in FIG. 2, the optical element holding member 52 has a tubular shape (for example, a cylindrical shape) in which a holding frame 521 and a loosely fitting part 522 are integrally formed. The optical element holding member 52 is configured so that the holding frame 521 is positioned at the one end along the center axis Ax of the tubular shape, and the loosely fitting part 522 is positioned at the other end.

The holding frame 521 is a portion that holds the optical element 53. As illustrated in FIG. 2, a second recessed part 5211 is formed on an inner peripheral side of one end of the holding frame 521, the second recessed part 5211 being recessed from the one end toward the other end into which the optical element 53 is loosely fitted.

The loosely fitting part 522 has an outer diameter dimension smaller than that of the first recessed part 511 (an outer diameter dimension smaller than an outer diameter dimension of the holding frame 521), and is loosely fitted into the first recessed part 511.

In the first embodiment, the optical element holding member 52 is configured of a ceramic material (coefficient of thermal expansion: $7.7\text{-}10.5 \times 10^{-6}/°$ C.) having chemical resistance. The optical element holding member 52 is configured to have rigidity higher than rigidity of the casing 51 through a material thereof, a thickness dimension in a radial direction, and the like.

On a side surface of the second recessed part 5211 and an outer peripheral surface of the loosely fitting part 522, as illustrated in FIG. 2, a metal layer 523 that may be brazed (corresponding to a metal part according to the present disclosure) is arranged (metalized).

The optical element 53 is a member that seals the opening at the one end of the casing 51 together with the optical element holding member 52.

In the first embodiment, the optical element 53 is configured of sapphire glass (coefficient of thermal expansion: $7.0\text{-}7.7 \times 10^{-6}/°$ C.) that is formed to have a flat plate shape and has chemical resistance.

That is, the optical element holding member 52 has a coefficient of thermal expansion closer to the coefficient of thermal expansion of the optical element 53 than the coefficient of thermal expansion of the casing 51.

On an outer peripheral surface of the optical element 53, as illustrated in FIG. 2, a metal layer 531 that can be brazed is arranged (metalized).

The optical element 53 is positioned in the vicinity of an exit pupil position of the base end (eyepiece part) of the insertion part 2 in a state in which the imaging device 5 for an endoscope is connected to the insertion part 2.

The lens unit 54 forms, on an imaging surface of the imaging part 55, the subject image the light of which is condensed by the insertion part 2 via the optical element 53. The lens unit 54 may be moved in an optical axis direction (a direction along the center axis Ax) by a driving motor (not illustrated) arranged in the casing 51 to adjust a focal distance and a focus.

The imaging part 55 images the inside of the living body under control by the control device 9. The imaging part 55 is configured by using a sensor chip obtained by integrally forming: an imaging element 551 (refer to FIG. 3) such as a charge coupled device (CCD) or a complementary metal oxide semiconductor (CMOS) that receives the subject image the light of which is condensed by the insertion part 2, the subject image being formed by the lens unit 54 via the optical element 53, and converts the subject image into an electric signal; and a signal processing unit (not illustrated) that performs signal processing (A/D conversion and the like) on the electric signal (analog signal) from the imaging element 551 and outputs an image signal. The imaging part 55 outputs the image signal (digital signal) after A/D conversion. The signal processing unit described above is not necessarily formed integrally with the imaging element 551, and may be formed separately from the imaging element 551.

Figure 3:
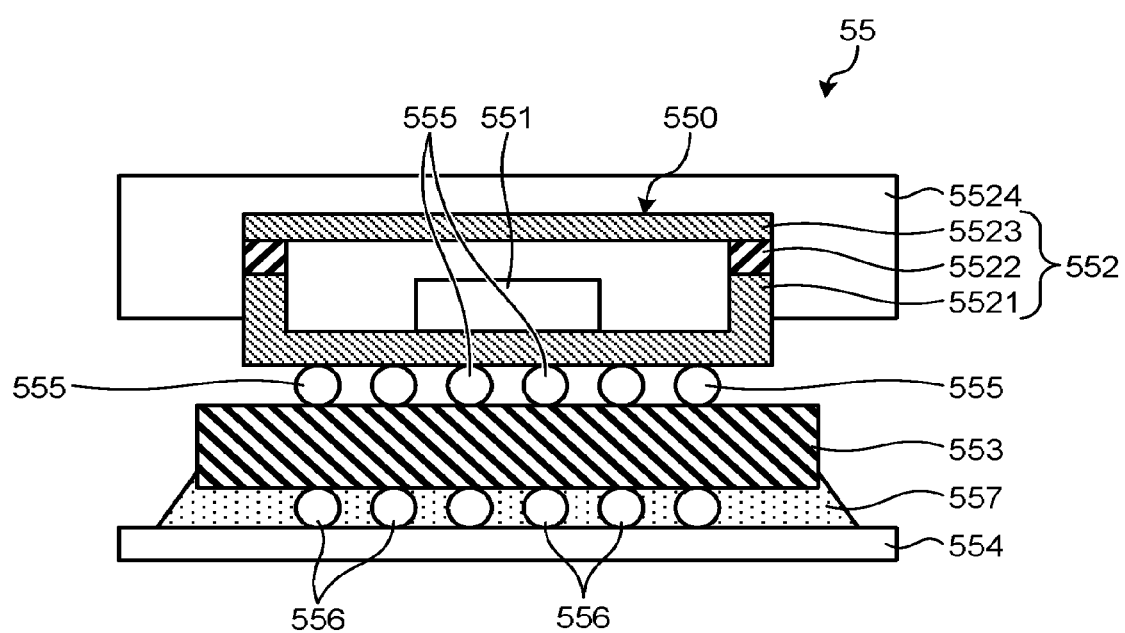
FIG. 3 is a diagram schematically illustrating a configuration of an imaging part illustrated in FIG. 2.

FIG. 3 is a diagram schematically illustrating a configuration of the imaging part 55.

As illustrated in FIG. 3, the imaging part 55 includes the imaging element 551, a holding unit 552, an intermediate member 553, a substrate 554, a first and second solder balls 555 and 556, and an underfill material 557.

The substrate 554 is a circuit board electrically connected to the hermetic connector described above. In the first embodiment, the substrate 554 is configured, for example, by using an organic material the thermal expansion coefficient of which in a direction along a mounting surface is equal to or larger than 12 ppm/° C. and equal to or smaller than 40 ppm/° C. under the ordinary temperature.

The imaging element 551 is implemented by using the CCD or the CMOS described above, and a plurality of pixels that receive light from the lens unit 54 are two-dimensionally arranged in a square form (arranged in a matrix) therein. The imaging element 551 then performs photoelectric conversion on light received by each pixel to generate an electric signal.

In the first embodiment, the number of effective pixels of the imaging element 551 is configured to be equal to or larger than 8 megapixels (for example, what is called 4K resolution of 3840×2160 pixels).

The imaging element 551 incorporates a circuit part that is electrically connected to the substrate 554 and transmits/receives a signal to/from the substrate 554.

The holding unit 552 is a housing that holds the imaging element 551 inside. As illustrated in FIG. 3, the holding unit 552 includes a holding part 5521, an annular part 5522, and a lid part 5523.

The holding part 5521 has a one-side bottomed tubular shape, and holds the imaging element 551 at the bottom thereof. The holding part 5521 has a thermal expansion coefficient smaller than the thermal expansion coefficient of the substrate 554. For example, the holding part 5521 is configured by using a ceramic material the thermal expansion coefficient of which in a direction along the mounting surface is equal to or larger than 4 ppm/° C. and equal to or smaller than 11 ppm/° C. under the ordinary temperature.

The annular part 5522 has an annular shape extending from an open end of the holding part 5521. The annular part 5522 is configured by using resin such as plastic, for example.

The lid part 5523 is formed in a plate shape, arranged on an end of the annular part 5522 opposite to the holding part 5521 side, and seals an opening having a bottomed tubular shape formed by the holding part 5521 and the annular part 5522. The lid part 5523 is configured of a material having light transmittivity, for example, glass.

A lens adapter 5524 (FIG. 3) is arranged on the holding unit 552, and the lens unit 54 is attached via the lens adapter 5524. The light from the lens unit 54 enters the imaging element 551 via the lid part 5523.

An image sensor part 550 is configured of the imaging element 551 and the holding unit 552 described above. Although the image sensor part 550 is configured of the imaging element 551 and the holding unit 552 in the first embodiment, the embodiment is not limited thereto. The image sensor part 550 may be configured of only the imaging element 551.

The intermediate member 553 is arranged between the image sensor part 550 and the substrate 554. The intermediate member 553 is, for example, a circuit board including electric wiring arranged inside and using ceramic, silicon, glass, epoxy resin including glass fibers, or the like as a base material. The thermal expansion coefficient of the intermediate member 553 is the same as the thermal expansion coefficient of the image sensor part 550, or is closer to the thermal expansion coefficient of the image sensor part 550 than that of the substrate 554. Specifically, the intermediate member 553 is configured by using a material having the thermal expansion coefficient equal to or larger than 95% of the thermal expansion coefficient of the holding part 5521 and equal to or smaller than an intermediate value between the thermal expansion coefficient of the holding part 5521 and the thermal expansion coefficient of the substrate 554.

The first solder ball 555 is arranged between the image sensor part 550 and the intermediate member 553. The first solder ball 555 electrically connects the image sensor part 550 (imaging element 551) to the intermediate member 553, and transmits a signal between the image sensor part 550 (imaging element 551) and the intermediate member 553. In the first embodiment, the first solder ball 555 electrically connects a solder pad (land) 5531 (refer to FIG. 4) arranged on the intermediate member 553 to a solder pad (land) 5501 (refer to FIG. 5) arranged on the image sensor part 550.

Figure 4:
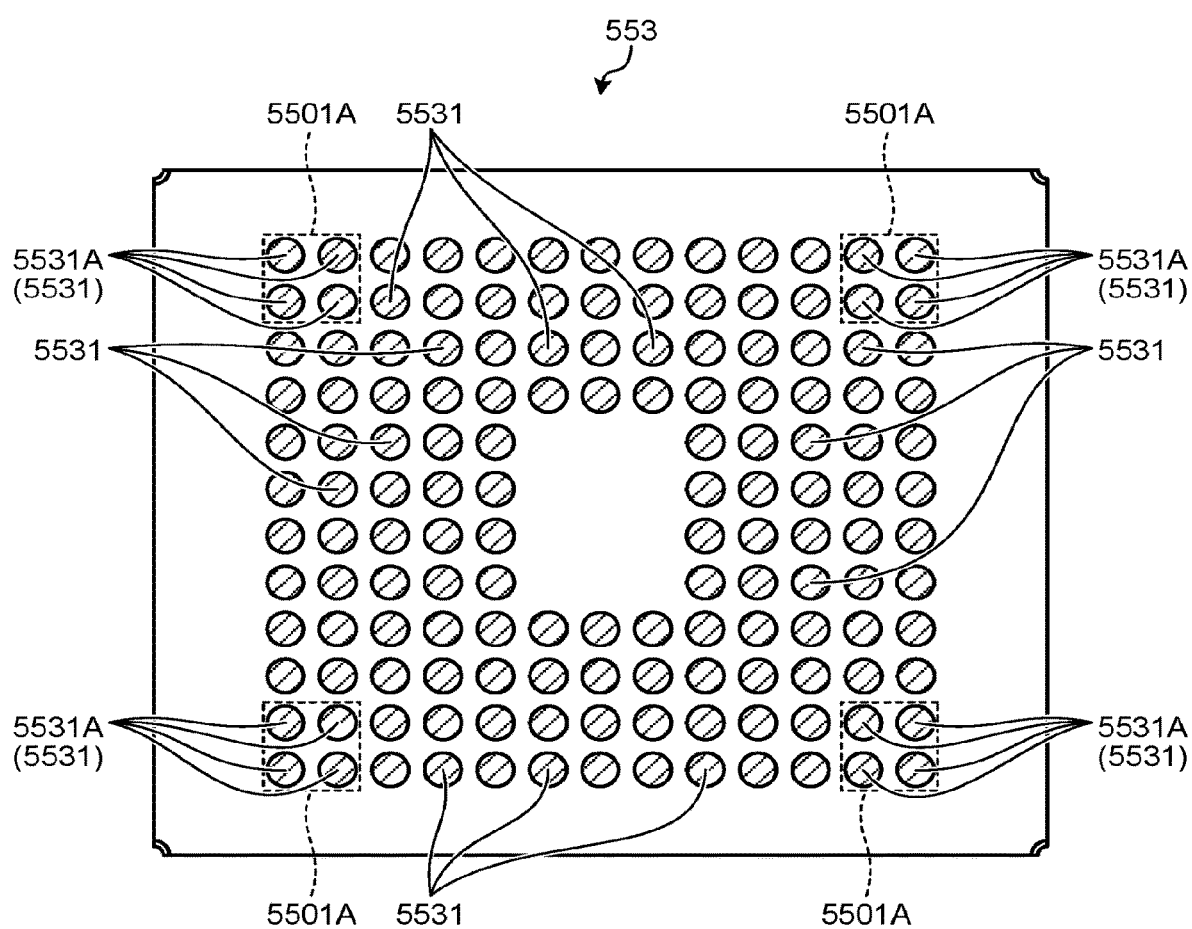
FIG. 4 is a diagram illustrating a solder pad as an intermediate member illustrated in FIG. 3.
Figure 5:
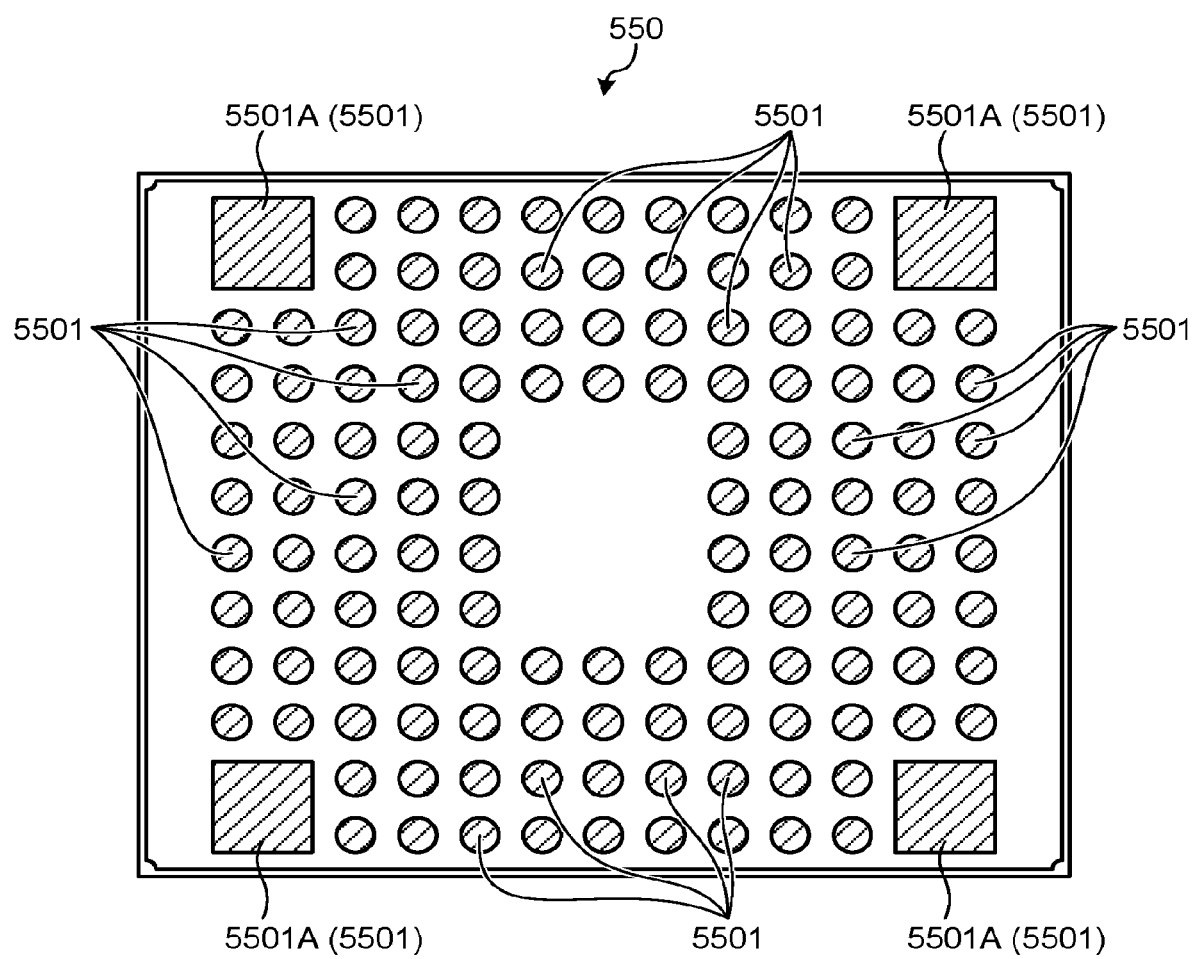
FIG. 5 is a diagram illustrating a solder pad of an image sensor part illustrated in FIG. 3.

FIG. 4 is a diagram illustrating the solder pad 5531 of the intermediate member 553. FIG. 5 is a diagram illustrating the solder pad 5501 of the image sensor part 550.

As illustrated in FIG. 4, solder pads 5531 arranged on the intermediate member 553 each have a circular shape, and are arranged in a matrix. On the other hand, as illustrated in FIG. 4, solder pads 5501 of the image sensor part 550 each have a circular shape corresponding to the solder pad 5531 arranged on the intermediate member 553, and are arranged in a matrix. Among the solder pads 5501, solder pads 5501A (hereinafter, referred to as reinforcing pads 5501A for convenience of explanation) positioned at four corners are each formed in a rectangular shape for covering four solder pads 5531A positioned at the four corners among the solder pads 5531 (FIG. 4, FIG. 5). That is, the reinforcing pads 5501A positioned at the four corners of the image sensor part 550 correspond to the respective four solder pads 5531A positioned at the four corners of the intermediate member 553.

The number of the first solder balls 555 to be arranged corresponds to the number of the solder pads 5531 arranged on the intermediate member 553, and the first solder ball 555 electrically connects the solder pad 5531 to the solder pad 5501. That is, at the four corners of the image sensor part 550 and the intermediate member 553, the four solder pads 5531A are electrically connected to the one reinforcing pad 5501A via the four first solder balls 555.

The second solder ball 556 is arranged between the intermediate member 553 and the substrate 554. The second solder ball 556 electrically connects the intermediate member 553 to the substrate 554, and transmits a signal between the intermediate member 553 and the substrate 554.

Each of the first and second solder balls 555 and 556 described above may be configured of only solder, or may be a solder ball containing a different material such as what is called a copper core solder ball in which copper is arranged in a core, for example, or what is called a resin core solder ball in which resin is arranged in a core. To reduce a failure in electrical connection caused by a difference in the thermal expansion coefficient between the image sensor part 550 and the substrate 554, it is preferable to use what is called a resin core solder ball as each of the first and second solder balls 555 and 556.

The underfill material 557 is filled in a space between the intermediate member 553 and the substrate 554 to fix the intermediate member 553 and the substrate 554, and prevent corrosion of the second solder ball 556 by surrounding the second solder ball 556. The underfill material 557 is a material having a modulus of elasticity smaller than that of the intermediate member 553 and the substrate 554. As the underfill material 557, preferred is a material having a glass transition temperature equal to or higher than 120° C., but the embodiment is not limited thereto. Under the ordinary temperature after curing, for example, the thermal expansion coefficient of the underfill material 557 is equal to or larger than 30 ppm/° C. and equal to or smaller than 50 ppm/° C.

The underfill material 557 may be configured by using a material having a thermal expansion coefficient value between the thermal expansion coefficient of the intermediate member 553 and the thermal expansion coefficient of the substrate 554. The underfill material 557 may also be filled in a space between the image sensor part 550 and the intermediate member 553.

The imaging device 5 for an endoscope is exposed to high temperature (for example, 120° C.) in sterilization treatment such as autoclaving in some cases. In such a case, the imaging part 55 is also exposed to high temperature, so that a failure may be caused in electrical connection between the image sensor part 550 and the substrate 554 due to a difference in the coefficient of thermal expansion among members configuring the imaging part 55.

In the first embodiment, the intermediate member 553 and the underfill material 557 are arranged between the image sensor part 550 and the substrate 554. Thus, when the device is exposed to high temperature in sterilization treatment such as autoclaving, it is prevented that stress is transmitted from the substrate 554 to the image sensor part 550 due to deformation of the substrate 554 caused by thermal expansion. Specifically, the stress corresponding to thermal expansion of the substrate 554 is transmitted to the underfill material 557, but absorbed by deformation of the underfill material 557. The stress is hardly transmitted to the image sensor part 550 because the thermal expansion coefficient of the intermediate member 553 is the same as or close to the thermal expansion coefficient of the image sensor part 550. Thus, connection between the image sensor part 550 and the intermediate member 553 (a joined state via the first solder ball 555) is not broken due to the stress caused by the substrate 554, and the image sensor part 550 may be connected to the substrate 554 in an electrically stable manner. Conversely, deformation of the image sensor part 550 caused by thermal expansion is prevented from being transmitted to the substrate 554 in the same manner.

In a case in which the device is exposed to high temperature in sterilization treatment such as autoclaving, and distortion is caused in the image sensor part 550 and the intermediate member 553 that are integrated with each other via the first solder ball 555 due to a difference in the thermal expansion coefficient between the image sensor part 550 and the intermediate member 553, distortion amounts at the four corners tend to be the largest.

In the first embodiment, a reinforcing pad 5501A having an area larger than that of the other solder pad 5501 is arranged at each of the four corners of the image sensor part 550. At the four corners of the image sensor part 550 and the intermediate member 553, the four solder pads 5531A are electrically connected to the one reinforcing pad 5501A via the four first solder balls 555.

Thus, the joined state of the image sensor part 550 and the intermediate member 553 at the four corners may be caused to be firm. Accordingly, the distortion amounts at the four corners may be reduced, and the image sensor part 550 may be stably electrically connected to the substrate 554 without breaking the connection between the image sensor part 550 and the intermediate member 553 (specifically, connection at the four corners).

In the first embodiment described above, the reinforcing pad 5501A having the area larger than that of the other solder pad 5501 is arranged at each of the four corners of the image sensor part 550, but the embodiment is not limited thereto. A reinforcing land having an area larger than that of the other solder pad 5531 may be arranged at each of the four corners of the intermediate member 553. In this case, the reinforcing land may be arranged on both of the image sensor part 550 and the intermediate member 553, or the reinforcing land may be arranged on only the intermediate member 553.

Method of Manufacturing Imaging Device for Endoscope

Next, the following describes a method of manufacturing the imaging device 5 for an endoscope described above.

First, an operator arranges the lens unit 54 and the imaging part 55 in the casing 51, and airtightly seals the opening at the other end of the casing 51 with a hermetic connector (not illustrated) by brazing (soldering) using solder.

Next, the operator fixes an inner peripheral surface of the holding frame 521 of the optical element holding member 52 (a side surface of the second recessed part 5211) to an outer peripheral surface of the optical element 53 by brazing (soldering) using the solder SD (FIG. 2) (first process).

Finally, the operator fixes an inner peripheral surface of one end of the casing 51 (a side surface of the first recessed part 511) to an outer peripheral surface of the loosely fitting part 522 of the optical element holding member 52 by brazing (soldering) using the solder SD (FIG. 2) (second process). Accordingly, the opening at the one end of the casing 51 is airtightly sealed by the optical element holding member 52 and the optical element 53.

The imaging device 5 for an endoscope according to the first embodiment described above includes the casing 51, the optical element holding member 52, and the optical element 53. The outer peripheral surface of the optical element 53 is brazed onto the inner peripheral surface of the optical element holding member 52, and the outer peripheral surface of the optical element holding member 52 is brazed onto the inner peripheral surface of the casing 51. In this case, the coefficient of thermal expansion of the optical element holding member 52 is closer to the coefficient of thermal expansion of the optical element 53 than the coefficient of thermal expansion of the casing 51.

That is, even when the optical element holding member 52 is brazed to the optical element 53 in a high temperature environment and the temperature is returned to the ordinary temperature, the coefficient of thermal expansion of the optical element holding member 52 is close to the coefficient of thermal expansion of the optical element 53, so that distortion may be reduced, the distortion being caused in the optical element 53 in accordance with a difference in the coefficient of thermal expansion between the members 52 and 53.

The optical element holding member 52 has rigidity higher than the rigidity of the casing 51 due to the material thereof, a thickness in a radial direction, and the like. Thus, even when the casing 51 is brazed to the optical element holding member 52 in a high temperature environment and the temperature is returned to the ordinary temperature, force from the casing 51 that may act on the optical element 53 via the optical element holding member 52 may be suppressed by the rigidity of the optical element holding member 52.

Accordingly, with the imaging device 5 for an endoscope according to the first embodiment, distortion caused in the optical element 53 may be reduced.

Specifically, deterioration in image quality corresponding to the distortion of the optical element 53 tends to be caused when the number of effective pixels of the imaging element 551 is equal to or larger than 4K resolution. In the first embodiment, when the number of effective pixels of the imaging element 551 is equal to or larger than 4K resolution, the deterioration in image quality may be effectively suppressed.

The coefficient of thermal expansion of the optical element holding member 52 is a value between the coefficient of thermal expansion of the optical element 53 and the coefficient of thermal expansion of the casing 51.

Thus, a difference between the coefficient of thermal expansion of the optical element holding member 52 and the coefficient of thermal expansion of the casing 51 may be reduced as compared with a case in which a value of the coefficient of thermal expansion of the optical element holding member 52 is smaller than that of the coefficient of thermal expansion of the optical element 53. In this way, by reducing the difference in the coefficient of thermal expansion between the members 51 and 52, an effect of reducing the distortion caused in the optical element 53 may be preferably achieved.

Second Embodiment

Next, the following describes a second embodiment of the present disclosure.

In the following description, the same component as that in the first embodiment is denoted by the same reference numeral, and detailed description thereof is not repeated or is simplified.

Figure 6:
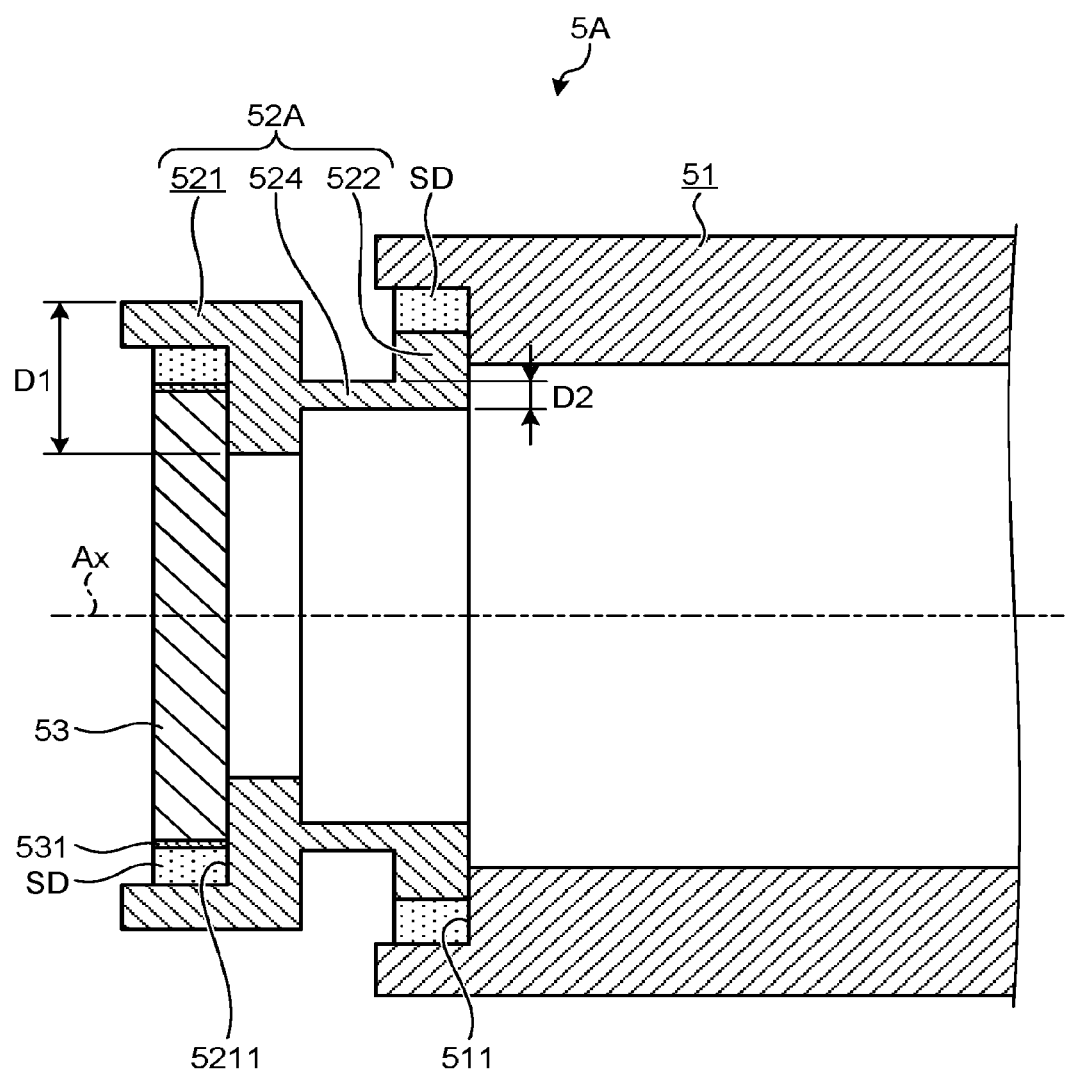
FIG. 6 is a diagram schematically illustrating a configuration of an imaging device for an endoscope according to a second embodiment of the present disclosure.

FIG. 6 is a diagram schematically illustrating a configuration of an imaging device 5A for an endoscope according to the second embodiment of the present disclosure. Specifically, FIG. 6 is a cross-sectional view corresponding to FIG. 2. In FIG. 6, the lens unit 54 and the imaging part 55 illustrated in FIG. 2 are not illustrated for convenience of explanation.

The imaging device 5A for an endoscope according to the second embodiment includes an optical element holding member 52A the shape and the material of which are different from those of the optical element holding member 52 in the imaging device 5 for an endoscope (FIG. 2) described in the first embodiment.

Specifically, as illustrated in FIG. 6, the optical element holding member 52A has a configuration in which a tubular (for example, cylindrical) distortion absorbing part 524 is interposed between the holding frame 521 and the loosely fitting part 522 differently from the optical element holding member 52 described in the first embodiment.

The distortion absorbing part 524 is a portion that absorbs distortion of the casing 51. The distortion absorbing part 524 has a thickness dimension D2 (FIG. 6) in a diameter direction smaller than a thickness dimension D1 (FIG. 6) in the radial direction of the holding frame 521. That is, the distortion absorbing part 524 is configured to be thinned to be elastically deformable, and absorbs distortion of the casing 51 by being elastically deformed.

In the second embodiment, the optical element holding member 52A is configured of Kovar alloy (coefficient of thermal expansion: $4.9 \times 10^{-6}/°C$.), Fe-42Ni—Cr—Ti (coefficient of thermal expansion: $6.8 \times 10^{-6}/°C$.), Incoloy (registered trademark) Alloy 909 (coefficient of thermal expansion: $7\text{-}8 \times 10^{-6}/°C$.), or Ti-6Al-4V (coefficient of thermal expansion: $8.8 \times 10^{-6}/°C$.).

That is, also in the second embodiment, the optical element holding member 52A has a coefficient of thermal expansion closer to the coefficient of thermal expansion of the optical element 53 than the coefficient of thermal expansion of the casing 51 similarly to the first embodiment described above.

The optical element holding member 52A is entirely configured of a metallic material (the entire optical element holding member 52A is a metal part according to the present disclosure). Thus, the metal layer 523 described in the first embodiment is not included in the optical element holding member 52A.

With the imaging device 5A for an endoscope according to the second embodiment described above, the following effect may be achieved in addition to the same effect as that in the first embodiment described above.

The optical element holding member 52A according to the second embodiment includes the distortion absorbing part 524. Thus, even when the casing 51 is brazed to the optical element holding member 52A in a high temperature environment and the temperature is returned to the ordinary temperature, force from the casing 51 that may act on the optical element 53 via the optical element holding member 52A may be absorbed by elastic deformation of the distortion absorbing part 524. Accordingly, distortion caused in the optical element 53 may be reduced similarly to the first embodiment described above.

Modification of Second Embodiment

Figure 7:
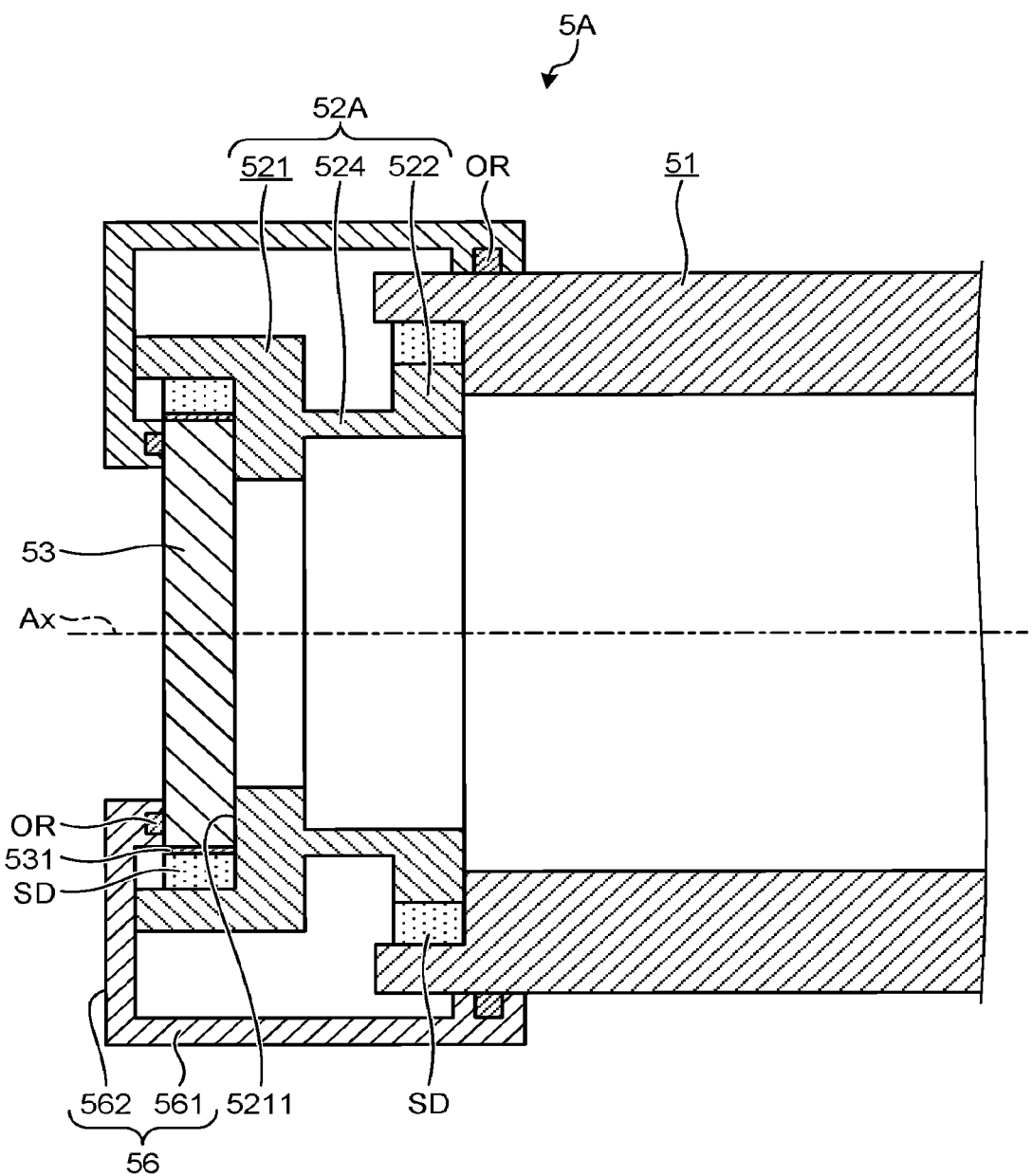
FIG. 7 is a diagram illustrating a modification of the second embodiment of the present disclosure.

FIG. 7 is a diagram illustrating a modification of the second embodiment of the present disclosure. Specifically, FIG. 7 is a cross-sectional view corresponding to FIG. 6.

In the second embodiment described above, when the optical element holding member 52A does not have chemical resistance, a covering member 56 may be arranged to cover the optical element holding member 52A as illustrated in FIG. 7.

As illustrated in FIG. 7, the covering member 56 includes a tubular part 561 and an overhang part 562.

The tubular part 561 has a tubular shape (for example, a cylindrical shape) into which one end of the imaging device 5A for an endoscope is inserted. The tubular part 561 has a length dimension longer than a length dimension in a direction of the center axis Ax of the optical element holding member 52A, and has an inner diameter dimension slightly larger than an outer diameter dimension of the casing 51. An O-ring OR is attached to an inner peripheral surface of the other end of the tubular part 561.

The overhang part 562 is formed in an annular shape overhanging from an inner peripheral surface of one end of the tubular part 561 toward the center axis Ax, and has an inner diameter dimension smaller than an outer diameter dimension of the optical element 53. The O-ring OR is attached to a back surface (surface on the other end side) of the overhang part 562.

In a state in which the covering member 56 is attached to one end of the imaging device 5A for an endoscope, a space between the tubular part 561 and the casing 51 is watertightly sealed with the O-ring OR, and a space between the overhang part 562 and the optical element 53 is watertightly sealed with the O-ring OR. That is, the optical element holding member 52A is watertightly sealed by the covering member 56, so that the optical element holding member 52A may be configured with a material not having chemical resistance.

Figure 8:
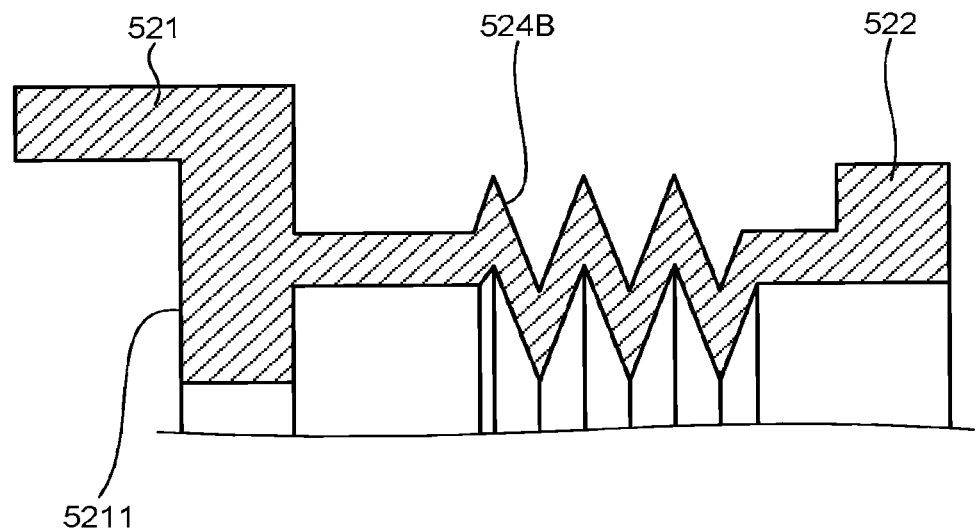
FIG. 8 is a diagram illustrating a modification of the second embodiment of the present disclosure.
Figure 9A:
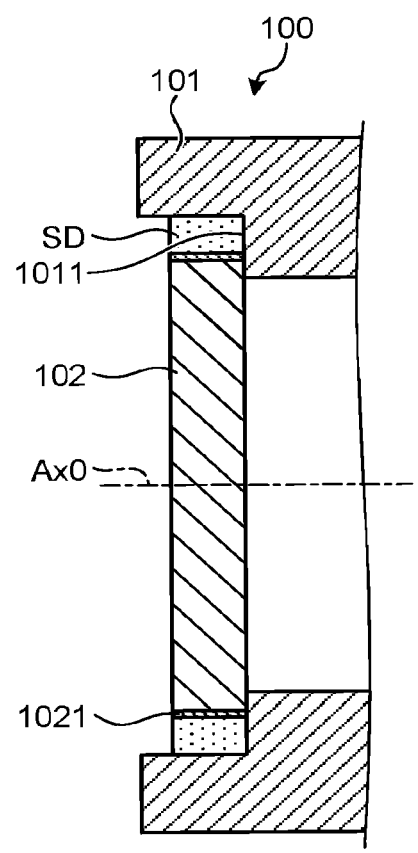
FIGS. 9A and 9B are diagrams for explaining a problem about an imaging device for an endoscope in the related art.
Figure 9B:
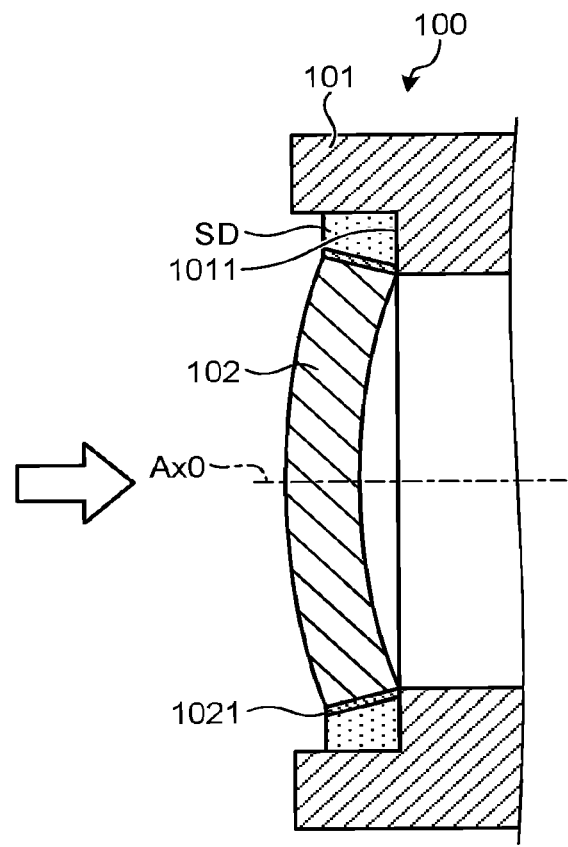

FIG. 8 is a diagram illustrating a modification of the second embodiment of the present disclosure. Specifically, FIG. 8 is an enlarged view of part of a cross section corresponding to FIG. 6.

The distortion absorbing part 524 is formed in a tubular shape (for example, a cylindrical shape) in the second embodiment described above, but the embodiment is not limited thereto. A distortion absorbing part 524B illustrated in FIG. 8 may be employed.

As illustrated in FIG. 8, the distortion absorbing part 524B is formed in a wavelike shape in a cross sectional view, that is, configured to be what is called bellows. That is, the distortion absorbing part 524B is configured as bellows to be deformable, and absorbs distortion of the casing 51 by being deformed similarly to the distortion absorbing part 524 described in the second embodiment.

In the second embodiment and the modification illustrated in FIG. 8 described above, the holding frame 521, the distortion absorbing part 524 (524B), and the loosely fitting part 522 are arranged in parallel along the center axis Ax, but the embodiment is not limited thereto. The holding frame 521, the distortion absorbing part 524 (524B), and the loosely fitting part 522 may be arranged in parallel in this order from an inner peripheral side along the radial direction.

Other Embodiments

The modes for carrying out the present disclosure have been described above. However, the present disclosure is not limited to only the first embodiment, the second embodiment, and the modifications thereof.

In the first embodiment, the second embodiment, and the modifications thereof, an exterior of the imaging device 5 (5A) for an endoscope is configured of two components, that is, the casing 51 and the optical element holding member 52 (52A). However, the embodiment is not limited thereto. That is, the number of the frame bodies may be equal to or larger than three so long as the first and the second frame bodies according to the present disclosure are included.

In the first embodiment, the second embodiment, and the modifications thereof, a material other than the material described in the first embodiment, the second embodiment, and the modifications thereof may be used as the material of the casing 51, the optical element holding member 52 (52A), and the optical element 53 so long as the condition that "the coefficient of thermal expansion of the optical element holding member 52 (52A) is closer to the coefficient of thermal expansion of the optical element 53 than the coefficient of thermal expansion of the casing 51" is satisfied.

The imaging device for an endoscope according to the present disclosure includes the first and the second frame bodies, and the optical element. The outer peripheral surface of the optical element is brazed onto the inner peripheral surface of the first frame body, and the outer peripheral surface of the first frame body is brazed onto the inner peripheral surface of the second frame body. In this case, the coefficient of thermal expansion of the first frame body is closer to the coefficient of thermal expansion of the optical element than the coefficient of thermal expansion of the second frame body.

That is, even when the first frame body is brazed to the optical element in a high temperature environment and the temperature is returned to the ordinary temperature, distortion caused in the optical element may be reduced in accordance with the difference in the coefficient of thermal expansion between the first frame body and the optical element because the coefficient of thermal expansion of the first frame body is close to the coefficient of thermal expansion of the optical element.

Because the first frame body is interposed between the second frame body and the optical element, even when the first frame body is brazed to the second frame body in a high temperature environment and the temperature is returned to the ordinary temperature, the first frame body may absorb or suppress force from the second frame body that may act on the optical element via the first frame body.

As described above, the imaging device for an endoscope according to the present disclosure may reduce distortion caused in the optical element.

The method of manufacturing the imaging device for an endoscope according to the present disclosure is a method of manufacturing the imaging device for an endoscope described above, so that the method produces the same effect as that of the imaging device for an endoscope described above.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An imaging device for an endoscope, the imaging device comprising:
   an optical element including a metal layer adapted to be brazed and arranged on an outer peripheral surface of the optical element;
   a first frame body including a metal part adapted to be brazed and arranged at least on an inner peripheral surface and an outer peripheral surface of the first frame body, the inner peripheral surface being brazed onto the outer peripheral surface of the optical element; and
   a second frame body including a metal part adapted to be brazed and arranged at least on an inner peripheral surface of the second frame body, the inner peripheral surface being brazed onto the outer peripheral surface of the first frame body, wherein
   a coefficient of thermal expansion of the first frame body is closer to a coefficient of thermal expansion of the optical element than a coefficient of thermal expansion of the second frame body.

2. The imaging device according to claim 1, wherein the first frame body comprises:
   a holding frame to which the outer peripheral surface of the optical element is brazed; and
   a distortion absorbing part that is positioned between the holding frame and the second frame body and absorbs distortion of the second frame body.

3. The imaging device according to claim 2, wherein the holding frame and the distortion absorbing part are arranged in parallel along a center axis of the first frame body, and
   a thickness dimension in a radial direction of the distortion absorbing part is smaller than a thickness dimension in a radial direction of the holding frame.

4. The imaging device according to claim 1, wherein the coefficient of thermal expansion of the first frame body is a value between the coefficient of thermal expansion of the optical element and the coefficient of thermal expansion of the second frame body.

5. The imaging device according to claim 1, wherein the optical element is sapphire glass.

6. A method of manufacturing an imaging device for an endoscope, the imaging device including an optical element including a metal layer adapted to be brazed and arranged on an outer peripheral surface of the metal layer, a first frame body including a metal part adapted to be brazed and arranged at least on an inner peripheral surface and an outer peripheral surface of the first frame body, and a second frame body including a metal part adapted to be brazed and arranged at least on an inner peripheral surface of the second frame body, the method comprising:
   brazing the outer peripheral surface of the optical element and the inner peripheral surface of the first frame body; and
   brazing the outer peripheral surface of the first frame body and the inner peripheral surface of the second frame body, wherein
   a coefficient of thermal expansion of the first frame body is closer to a coefficient of thermal expansion of the optical element than a coefficient of thermal expansion of the second frame body.

* * * * *